US010555524B2

(12) United States Patent
LeFiles et al.

(10) Patent No.: US 10,555,524 B2
(45) Date of Patent: Feb. 11, 2020

(54) PESTICIDAL COMPOSITIONS AND RELATED METHODS

(71) Applicant: CJB Applied Technologies LLC, Valdosta, GA (US)

(72) Inventors: James Holt LeFiles, Valdosta, GA (US); Paul Andrew Patterson, Valdosta, GA (US)

(73) Assignee: CJB Applied Technologies, Valdosta, GA (US)

( * ) Notice: Subject to any disclaimer, the term of this patent is extended or adjusted under 35 U.S.C. 154(b) by 0 days.

(21) Appl. No.: 16/185,578

(22) Filed: Nov. 9, 2018

(65) Prior Publication Data

US 2019/0133127 A1 May 9, 2019

Related U.S. Application Data

(60) Provisional application No. 62/583,626, filed on Nov. 9, 2017, provisional application No. 62/643,215, filed on Mar. 15, 2018.

(51) Int. Cl.
| | | |
|---|---|---|
| *A01N 43/54* | (2006.01) | |
| *A01N 25/04* | (2006.01) | |
| *A01N 43/56* | (2006.01) | |
| *A01N 43/653* | (2006.01) | |
| *A01N 43/40* | (2006.01) | |

(52) U.S. Cl.
CPC ............. *A01N 43/54* (2013.01); *A01N 25/04* (2013.01); *A01N 43/56* (2013.01); *A01N 43/653* (2013.01)

(58) Field of Classification Search
CPC ...... A01N 43/54; A01N 25/04; A01N 43/653; A01N 43/56; A01N 47/24; A01N 43/40
See application file for complete search history.

(56) References Cited

U.S. PATENT DOCUMENTS

| | | |
|---|---|---|
| 6,124,301 A | 9/2000 | Aven et al. |
| 10,130,091 B2 | 11/2018 | Brown et al. |
| 2004/0106523 A1 | 6/2004 | Stridde et al. |
| 2011/0224076 A1 | 9/2011 | Sowa |
| 2012/0015813 A1 | 1/2012 | Nomura et al. |
| 2015/0004109 A1 | 1/2015 | Kurkal-Siebert et al. |
| 2015/0051077 A1 | 2/2015 | Schnabel et al. |
| 2016/0183528 A1 | 6/2016 | Hopkins et al. |

OTHER PUBLICATIONS

International Search Report for PCT/US18/60008, dated Feb. 4, 2019.
Brent, K.J. and Hollomon, D.W., "Fungicide Resistance in Crop Pathogens: How can it be Managed", Croplife International, 2nd Revised Edition, Published by the Fungicide Resistance Action Committee (2007), Brussels, Belgium, pp. 1-60.

*Primary Examiner* — Sahar Javanmard
(74) *Attorney, Agent, or Firm* — Barnes & Thornburg LLP

(57) ABSTRACT

Pesticidal compositions are provided that include at least one pesticidal active ingredient and at least one organic solvent. Adjuvant compositions are provided for use with at least one pesticidal active ingredient that include at least one organic solvent. Methods of producing an adjuvant composition and pesticidal composition are also provided.

8 Claims, No Drawings

PESTICIDAL COMPOSITIONS AND RELATED METHODS

CROSS-REFERENCE TO RELATED APPLICATIONS

The present application claims priority to U.S. provisional patent application Ser. No. 62/583,626, filed Nov. 9, 2017 and U.S. provisional patent application Ser. No. 62/643,215, filed Mar. 15, 2018.

BACKGROUND OF INVENTION

The control of various pests such as, for example, fungal infestations and bacterial infections continues to be a major problem in pesticidal and horticultural fields. Particularly, genetic changes in pathogenic bacteria and fungi have generated resistance to the efficacy of many types of active ingredients. Fungicide and bactericide resistance have particularly become a major challenge rendering some pesticidal compositions containing a fungicide or bactericide less efficacious against certain fungi and bacteria. In an attempt to overcome these challenges, the end-user normally adds an adjuvant to the spray mixture to improve the performance of pesticidals, however, such adjuvants may increase the cost and impact crop yield as well as the environment. Thus, there remains a need for low toxicity and crop safe adjuvant compositions that increase the efficacy of pesticidal active ingredients.

SUMMARY OF INVENTION

According to one aspect, a pesticidal composition is provided. The pesticidal composition includes at least one pesticidal active ingredient and at least one organic solvent such as propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, and any combination thereof. According to one embodiment, the at least one organic solvent is benzyl acetate. According to one embodiment, the pesticidal composition further includes water, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof. According to one embodiment, the at least one pesticidal active ingredient is a fungicide, bactericide, herbicide, insecticide, pesticide, plant growth regulator, or biopesticide. According to one embodiment, the at least one pesticidal active ingredient is a fungicide. According to one embodiment, the pesticidal composition includes from about from about 5% w/w to about 70% w/w of the at least one pesticidal active ingredient, from about 39% w/w to about 93% w/w of the at least one organic solvent; and from about 2% w/w to about 80% w/w of water, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof.

According to one aspect, an adjuvant composition is provided. The adjuvant composition includes at least one organic solvent such as propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, and any combination thereof. The adjuvant composition, when combined with at least one pesticidal active ingredient, increases the efficacy of the at least one pesticidal active ingredient by at least about 25% compared to the at least one pesticidal active ingredient alone. According to one embodiment, the at least one organic solvent is benzyl acetate. According to one embodiment, the adjuvant composition further includes water, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof. According to one embodiment, adjuvant includes about 0.0% v/v to about 2.0% v/v water, about 0.0% v/v to about 2.0% v/v potassium hydroxide, about 0.0% v/v to about 2.0% v/v citric acid, about 0.0% v/v to about 2.0% v/v cocodimethylamine, about 20% v/v to about 99% v/v of at least one organic solvent, and about 10% v/v to about 70% v/v of at least one surfactant. According to one embodiment, the at least one organic solvent is benzyl acetate, propylene carbonate, N-methylpyrrolidone, or any combination thereof. According to one embodiment, the at least one surfactant is cocodimethylamine, polyoxyethylene sorbitan monolaurate. According to one embodiment, the at least one pesticidal active ingredient is a fungicide, bactericide, herbicide, insecticide, pesticide, plant growth regulator, or biopesticide. According to one embodiment, the at least one pesticidal active ingredient is a fungicide.

According to another aspect, a method of producing an adjuvant composition is provided. The method includes the step of introducing at least one organic solvent to a container. The at least one organic solvent includes propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, or any combination thereof. The method may further include the step of introducing at least one additional component to the container, wherein the at least one additional component is water, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof. The method may further include the step of attaching at least one set of instructions to the container. The at least one organic solvent is introduced to the container in an amount such that the entire container contents may be added directly to a spray tank comprising at least one pesticidal active ingredient for form a tank mix pesticidal composition. According to one embodiment, the at least one organic solvent is benzyl acetate. According to one embodiment, the adjuvant composition increases the efficacy of the at least one pesticidal active ingredient by at least about 25% compared to the at least one pesticidal active ingredient alone. According to one embodiment, the at least one pesticidal active ingredient is a fungicide, bactericide, herbicide, insecticide, pesticide, plant growth regulator, or biopesticide.

According to one aspect, a tank mix pesticidal composition is provided. The tank mix pesticidal composition includes at least one pesticidal active ingredient, at least one organic solvent, and water, spray oil, or a combination of water and spray oil. The at least one organic solvent is propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, or any combination thereof. According to one embodiment, the tank mix includes from about 0.2% v/v to about 5% v/v of at least one pesticidal active ingredient; from about 0.2% v/v to about 2 v/v % of at least one organic solvent; and from about 80% v/v to about 99% of water, spray oil, or a combination of water and spray oil. According to one embodiment, the at least one active ingredient is a fungicide, bactericide, herbicide, insecticide, pesticide, or biopesticide. According to one embodiment, the organic solvent is benzyl acetate.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, the term "adjuvant" refers to one or more organic solvents that improve the desired performance of a pesticidal active ingredient.

As used herein, the term "pesticide" or "pesticidal" refers to crop use, turf use, ornamental use, homeowner use or similar use.

Pesticidal compositions for improving the desired performance of a pesticidal active ingredient are provided. The pesticidal compositions described herein include at least one organic solvent, at least one active ingredient and, optionally, one or more additional components as provided herein. According to one embodiment, the pesticidal compositions as provided herein are added to a spray tank such that a stable tank mix pesticidal composition (i.e., spray tank mixture) is formed when the pesticidal composition and any other additional optional ingredients, such as water or spray oil, are combined in the spray tank.

According to one embodiment, the pesticidal compositions as provided herein are formulated as an emulsifiable concentrate formulation, aqueous suspension concentrate (suspension concentrate), emulsion in water formulation, dry flowable, water dispersible granule, wettable powder, soluble powder, oil dispersion, or concentrated aqueous solution.

An organic solvent as provided herein is preferably not phytotoxic, approved for crop use by the Environmental Protection Agency (EPA) and safe for end user mixing. Suitable organic solvents include, but are not limited to, organic compounds within the chemical classes of carbonates, ester compounds, amide compounds, ketone compounds, and alcohol compounds. According to a particular embodiment, the organic solvent is propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, or any combination thereof.

According to a particular embodiment, the at least one organic solvent provided herein is benzyl acetate. The benzyl acetate as provided herein may be commercially available from various sources such as, for example, Sigma Aldrich. The benzyl acetate as provided herein may also be derived from a natural source such as, for example, essential oils. Suitable essential oil sources include, but are not limited to, jasmine oil, ylang ylan oil, neroli oil, or any combination thereof.

According to a particular embodiment, the organic solvent is propylene carbonate. According to another particular embodiment, the organic solvent is N-methylpyrrolidone.

Other suitable organic solvents include, but are not limited to, acetate esters such as, for example, n-butyl acetate, iso-butyl acetate, n-pentyl acetate, iso-pentyl acetate, n-hexyl acetate, iso-hexyl acetate, cyclohexyl acetate, phenyl acetate, n-heptyl acetate, iso-heptyl acetate, cyclohexylmethyl acetate, benzyl alcohol, benzyl acetate, benzyl salicylate, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, 1,2-butylene carbonate, diethylene glycol butyl ether, diethylene glycol butyl ether acetate, dibasic ester mixture, dimethyl sulfoxide, dipropylene glycol methyl ether, ethylene glycol butyl ether, ethylene carbonate, 3-ethoxy ethyl proprionate, ethylene glycol diacetate, furfuryl alcohol, gamma-butyrolactone, methyl ethyl ketone, methyl isoamyl ketone, n-amy acetate, n-methyl-2-pyrrolione, propylene glycol butyl ether, propylene carbonate, propylene, glycol methyl ether, propylene glycol methyl ether acetate, triethylene glycol, glycol diether, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, amyl alcohol, tetrahydrofurfuryl alcohol, hexanol, octanol, ethylene glycol, propylene glycol, glycerol, N-methyl-2-pyrrolidone, glycerol, pentaerythritol, dimethyl sulfoxide, dimethyl formamide, glymes, acetone, Atlox™ 4915, Atlox™ PN-100, Zephrym™ PD3315, any of the Tween™ L Series compounds, and combinations thereof.

According to one embodiment, the pesticidal compositions as provided herein include typically at least from about 39% by weight (w/w) to about 93% by weight (w/w) of at least one organic solvent as provided herein. According to one embodiment, the pesticidal composition includes typically at least about 45% by weight (w/w) of at least one organic solvent as provided herein. According to one embodiment, the pesticidal composition includes typically at least about 55% by weight (w/w) of at least one organic solvent as provided herein. According to one embodiment, the pesticidal composition includes typically at least about 65% by weight (w/w) of at least one organic solvent as provided herein. According to one embodiment, the pesticidal composition includes typically at least about 75% by weight (w/w) of at least one organic solvent as provided herein. According to one embodiment, the pesticidal composition includes typically at least about 85% by weight (w/w) of at least one organic solvent as provided herein. According to one embodiment, the pesticidal composition includes typically at least about 90% by weight (w/w) of at least one organic solvent as provided herein. According to one embodiment, the pesticidal composition includes typically at least about 93% by weight (w/w) of at least one organic solvent as provided herein.

According to one embodiment, the pesticidal compositions as provided herein include typically from about 5% by weight (w/w) to about 70% by weight (w/w) of the at least one pesticidal active ingredient as provided herein. According to one embodiment, the pesticidal composition includes typically at least about 10% by weight (w/w) of at least one pesticidal active ingredient as provided herein. According to one embodiment, the pesticidal composition includes typically at least about 20% by weight (w/w) of at least one pesticidal active ingredient as provided herein. According to one embodiment, the pesticidal composition includes typically at least about 30% by weight (w/w) of at least one pesticidal active ingredient as provided herein. According to one embodiment, the pesticidal composition includes typically at least about 40% by weight (w/w) of at least one pesticidal active ingredient as provided herein. According to one embodiment, the pesticidal composition includes typically at least about 50% by weight (w/w) of at least one pesticidal active ingredient as provided herein. According to one embodiment, the pesticidal composition includes typically at least about 60% by weight (w/w) of at least one pesticidal active ingredient as provided herein.

According to one embodiment, the pesticidal compositions as provided herein include typically from about 2% by weight (w/w) to about 80% by weight (w/w) of water, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof.

As provided herein, a pesticidal active ingredient is a fungicide, bactericide, herbicide, insecticide, pesticide, biopesticide, plant growth regulator or any combination thereof. The at least one pesticidal active ingredient may be any active ingredient approved by the Environmental Protection Agency and registered under the Federal Insecticide, Fungicide, and Rodenticide Act (FIFRA).

According to one embodiment, the at least one pesticidal active ingredient is a fungicide. According to one embodiment, the fungicide is within the family of strobilurin fungicides. According to a particular embodiment, the at least one pesticidal active ingredient is a fungicide such as, for example, azoxystrobin. According to another embodiment, the at least one pesticidal active ingredient is a fungicide such as, for example, iprodione, oxytetracycline, bifujunzhi, coumethoxystrobin, coumoxystrobin, dimoxystrobin, enestroburin, enoxastrobin, fenaminstrobin, fenoxystrobin, flufenoxystrobin, fluoxastrobin, jiaxiangjunzhi, kresoxim-methyl, mandestrobin, metominostrobin, orysastrobin, picoxystrobin, pyraclostrobin, pyrametostrobin, pyraoxystrobin, triclopyricarb, trifloxystrobin, methyl 2-[2-(2,5-dimethylphenyloxymethyl)phenyl]-3-methoxyacrylate, pyribencarb, triclopyricarb/chlorodincarb, famoxadon, fenamidon, cyazofamid, amisulbrom, benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthio-biphenyl-2-yl)-3-difluoromethyl-1-methyl-1H-pyrazole-4-carboxamide, N-(2-(1,3,3-trimethylbutyl)phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, diflumetorim, binapacryl, dinobuton, dinocap, meptyl-dinocap, fluazinam, ferimzone, ametoctradin, silthiofam, azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, imazalil, pefurazoate, prochloraz, triflumizole, pyrimidines, fenarimol, nuarimol, pyrifenox, triforine, aldimorph, dodemorph, dodemorph acetate, fenpropimorph, tridemorph, fenpropidin, piperalin, spiroxamine, fenhexamid, benalaxyl, benalaxyl-M, kiralaxyl, metalaxyl, metalaxyl-M (mefenoxam), ofurace, oxadixyl, hymexazole, octhilinone, oxolinic acid, bupirimate, benomyl, carbendazim, fuberidazole, thiabendazole, thiophanate-methyl, 5-chloro-7-(4-methyl-piperidin-1-yl)-6-(2,4,6-trifluorophenyl)-[1,2,4]triazolo[1,5-a]pyrimidine, diethofencarb, ethaboxam, pencycuron, fluopicolid, zoxamid, metrafenon, pyriofenon, cyprodinil, mepanipyrim, pyrimethanil, fluoroimide, iprodione, procymidone, vinclozolin, fenpiclonil, fludioxonil, quinoxyfen, edifenphos, iprobenfos, pyrazophos, isoprothiolane, dicloran, quintozene, tecnazene, tolclofos-methyl, biphenyl, chloroneb, etridiazole, dimethomorph, flumorph, mandipropamid, pyrimorph, benthiavalicarb, iprovalicarb, valifenalate and 4-fluorophenyl N-(1-(1-(4-cyanophenyl)ethanesulfonyl)but-2-yl)carbamate, propamocarb, propamocarb hydrochloride, ferbam, mancozeb, maneb, metiram, propineb, thiram, zineb, ziram, anilazine, chlorothalonil, captafol, captan, folpet, dichlofluanid, dichlorophen, flusulfamide, hexachlorobenzene, pentachlorophenol, phthalid, tolylfluanid, N-(4-chloro-2-nitrophenyl)-N-ethyl-4-methylbenzenesulfonamide, guanidine, dithianon, validamycin, polyoxin B, pyroquilon, tricyclazole, carpropamid, dicyclomet, fenoxanil, and mixtures thereof.

According to one embodiment, the at least one pesticidal active ingredient is a herbicide. Suitable herbicides include those from all of the major families of herbicide chemistry including but not limited to sulfonylurea, triazine, uracil, imidazoline, pyridine, and urea. Suitable herbicides include but are not limited to, 2,4-D, clyopyralid, dicamba, fosamine, glyphosate, imazapyr, hexazinone, imazapyr, metsulfuron methyl, pcloram, sulfometuron methyl and other sulfonylurea compounds, triclopyr, ethofumesate, bifenzate, metribuzin, fenmedipham, desmedipham, thidiazuron, diuron, quinclorac, clodinafop, fenoxaprop, tralkoxydim, prosulfocarb, triasulfuron, prosulfuron, amidosulfuron, iodosulfuron, chlorsulfuron, flupyrsulfuron, mesosulfuron, metsulfuron, sulfosulfuron, thifensulfuron, tribenuron, tritosulfuron, florasulam, metosulam, flumetsulam, pyroxsulam, dichlorprop-p, MCPA, mecoprop, mecoprop-p, MCPB, clopyralid, bromoxynil, bromoxynil-octanoate, ioxynil, ioxynil-octanoate, fluroxypyr, trifluralin, diflufenican, picolinafen, pendimethalin and triallate, tralkoxydim, triasulfuron, diflufenican, florasulam, pyroxsulam, pyroxsulam, bipyridyliums, diphenyl ethers (nitrophenyl ethers), triazines, uracils, phenylureas, nitriles, Stam (3',4'-dichloropropionanilide, DCPA) and Alachlor (2-chloro-2',6'-diethyl-N-(methoxymethyl)-acetanilide), DCMU (3-(3,4-dichlorophenyl)-1,1-dimethylurea) and Rinuron (3-(3,4-dichlorophenyl)-1-methoxy-1-methylurea), thifensulfuromnethyl(methyl-3-(4-methoxy-6-methyl-1,3,5-triazin-2-ylcarbamoylsulfamoyl)-2-tanoate), Flazesulfuron (1-(4,6-dimethoxy pyrimidin-2-yl)-3-(3-trifluoromethyl-2-pyridylsulfonyl-)urea), Paraquat dichloride (1,1'-dimethyl-4,4'-bipyridinium dichloride), Diquat dibromide (6,7-dihydrodipyride[1,2-a:2',1'c]-pyrazinediium dibromide), Bromacil (5-bromo-3-sec-butyl-6-methyluracil), Gesatop (2-chloro-4,6-bis(ethylamino)-1,3,5-triazine), Simetryn (2,4-bis(ethylamino)-6-methylthio-1,3,5-triazine), DBN (2,6-dichlorobenzonitrile-), Trifluralin (alpha,alpha, alpha-trifluoro-2,6-dinitro-N,N-dipropyl-p-toluidine), Thiobencarb (Saturn) (S-p-chlorobenzyl diethylthiocarbamate), MCC (methyl-3,4-dichlorocarbe-nylate, NIP (2,4-dichlorophenyl-p-nitro-phenyl ether), PCP (sodium pentachlorophenoxide), MDBA (3,6-dichloro-2-methoxybenzoic acid dimethylamine salt), 2,4-D sodium salt (sodium 2,4-dichlorophenoxyacetate), 2,4 D Esters, Mapica ([4-chloro-o-toluyl)oxy]aceto-o-chloroanilide, Bialaphos (sodium salt of L-2-amino-4-[hydroxy(methyl)phosphi-noyl]-butylyl-alanyl-N-alanine), Glufosinate (ammonium DL-homoalanin-4-yl(methyl)phosphinate), TCA sodium salt (sodium trichloronate), and combinations thereof.

According to one embodiment, the at least one pesticidal active ingredient is an insecticide. Suitable insecticides include, but are not limited to, organochlorines, organophosphates, azinphos-methyl, azinphos-ethyl, chlorpyrifos, chlorpyrifos-methyl, chlorfenvinphos, diazinon, dimethylvinphos, dioxabenzofos, disulfoton, ethion, EPN, fenitrothion, fenthion, heptenophos, isoxathion, malathion, methidathion, methyl-parathion, paraoxon, parathion, phenthoate, phosalone, phosmet, phorate, phoxim, pirimiphos-methyl, profenofos, prothiofos, primiphos-ethyl, pyraclofos, pyridaphenthion, sulprofos, triazophos, trichlorfon, tetrachlorvinphos, vamidothion; carbamates, alanycarb, benfuracarb, bendiocarb, carbaryl, carbofuran, carbosulfan, fenoxycarb, furathiocarb, indoxacarb, methiocarb, pirimicarb, propoxur, thiodicarb, triazamate, organosulfurs, carbamates, formamidines, dinitrophenols, organotins, pyrethroids, acrinathrin, allethrin, bioallethrin, barthrin, bioethanomethrin, cyclethrin, bifenthrin, cyfluthrin, beta-cyfluthrin, cycloprothrin, cypermethrin, cyphenothrin, deltamethrin, dimefluthrin, dimethrin, empenthrin, esfenvalerate, etofenprox, flufenprox, halfenprox, protifenbute, fenpirithrin, fenfluthrin, fenpropathrin, fenvalerate, flucythrinate, furethrin, imiprothrin, metofluthrin, cyhalothrin, lambda-cyhalothrin, gamma-cyhalothrin, permethrin, biopermethrin, transpermethrin, phenothrin, prallethrin, profluthrin, pyresmethrin, resmethrin, bioresmethrin, cismethrin, silafluofen, fluvalinate, tau-fluvalinate, tefluthrin, terallethrin, tetramethrin, tralomethrin, alpha-cypermethrin, beta-cypermethrin, theta-cypermethrin, zeta-cypermethrin, permethrin, nicotinoids, spinosyns, pyrazoles, pyridazinones, quinazolines, abamectin, acequinocyl, acetamiprid, amitraz, azadirachtin, bensultap, bifenazate, cartap, chlorfenapyr, chlordimeform, diafenthiuron, dinetofuran, diofenolan, emamectin, endosulfan, ethiprole, fenazaquin, fipronil, formetanate, formetanate hydrochloride, gamma-HCH, hydramethylnon, imidacloprid, indoxacarb, isoprocarb, metolcarb, pyridaben, pymetrozine, spinosad, tebufenpyrad, thiamethoxam, thiocyclam, pyridalyl, flonicamid, fluacypyrim, milbemectin, spiromesifen, flupyrazofos, tolfenpyrad, flubendiamide, bistrifluoron, benclothiaz, pyrafluprole, pyriprole, amidoflumet, flufenerim, cyflumetofen, acequinocyl, lepimectin, profluthrin, dimefluthrin, xylylcarb, bromopropylate, spirodiclofen, clofentezine, fenpyroxymate, hexythiazox, Fenvalerate (alpha-cyano-3-phenoxybe-nzyl-2-(4-chlorophenyl)-3-methylbutanoate),
Baythroid (cyano-4-fluoro-3-phenoxybenzyl-3-(2,2-dichlorovinyl)-2,2-dimethylcyclopr-opanecarboxylate), DDVP (2,2-dichlorovinyldimethyl phosphate), Sumithion (MEP) (dimethyl 4-nitro-m-tolyl phosphorothioate), Malathion (S-1,2-bis(ethoxycarbonyl)et-hyldimethyl phosphorodithioate), Dimethoate (dimethyl S—(N-methylcarbamoylmethyl) phosphorodithioate), Elsan (S-[alpha-(ethoxycarbonyl)benzyl]dimethyl phosphorodithioate), Baycid (dimethyl 4-methylthio-m-tolyl phosphorothioate), Bassa (O-sec-butylphenyl methylcarbamate), MTMC (m-tolylmethylcarbamate), Meopal (3,4-dimethylphenyl-N-methylcarbamate), NAC (1-naphthyl methylcarbamate), Methomyl (S-methyl-N-(methylcarbamoyloxy)thioacetimidate), Cartap (SS'-2-dimethylamino trimethylene bis-(thiocarbamate), cinnamon leaf oil, oregano oil, polyketide, pyrethrum, ryanodine, spinosad, spinosyn A, spinosyn D, thymol, *Bacillus sphaericus, Bacillus thuringiensis, Bacillus thuringiensis aizawi, Bacillus thuringiensis israelensis, Bacillus thuringiensis kurstaki, Bacillus thuringiensis tenebrionis*, nuclear polyhedrosis virus, granulovirus, lecanicillium lecanii, diatomaceous earth, borate, borax, boric acid, and mixtures thereof.

According to one embodiment, the at least one pesticidal active ingredient is a bactericide. Suitable bactericides include any pesticidally acceptable bactericide. Such bactericides include, but are not limited to, validamycin, streptomycin, salmycin, envviromycin, 2-phenylphenol, thymol, 4-tert-amylphenol, 4-chloro-3-methylphenol, 4-chloro-2-benzylphenol and 4-chloro-3,5-dimethylphenol, 1,2-benzisothiazol-3(2H)-one (BIT), carbendazim, chlorotoluron, mixtures of 5-chloro-2-methyl-4-isothiazolin-3-one with 2-methyl-4-isothiazolin-3-one, 2,2-dibromo-3-nitrilopropionamide (DBNPA), fluometuron, 3-iodo-2-propynylbutyl carbamate (IPBC), isoproturon, 2-n-octyl-4-isothiazolin-3-one (OIT), prometryn, and propiconazole.

According to one embodiment, the at least one pesticidal active ingredient is at least one biopesticide. Suitable biopesticides includes those derived from natural products (naturally occurring), such as animals, plants, bacteria (e.g., Howler from AgBiome), and certain minerals. According to one embodiment, the at least one biopesticide is synthetic (not naturally occurring). The at least one biopesticide may be used to control pests or the microorganisms that control pests. Suitable biopesticides include, but are not limited to, the biopesticides registered as biopesticide active ingredients with the United States Environmental Protection Agency. Such suitable biopesticides include, but are not limited to, cold pressed neem oil, ulocladium oudemansii, lavandulyl senecioate, calcium acetae, 2-methyl-1-butanol, trichoderma asperellum, trichoderma gamsii, laminarin food use fungicide, (E,Z)-7,9-Dodecadien-1-yl acetate, abscisic acid, (Z,Z,E)-7,11,13-hexadecatrienal, coat protein gene of plum pox virus, homobrassinolide, chenopodium ambrosoides, trichoderma hamatum isolate, (Z,Z,E)-3,8,11-tetradecatrienyl acetate, cry1Ac in MON 87701, *Bacillus thuringiensis* Vip3Aa20, hydrogentated catmint oil, n-tetradecyl acetate, iron HEDTA, heptyl butyrate, sodium ferric EDTA, oriental mustard seed, Z-7-tetradeced-2-one, L-Lactic Acid, *Pasteuria usgae*, candida oleophila strain O, yeast, trimethylamine, indole, L-carvone, fox urine, calcium lactate, chenopodium ambrosioides, b. firmus, *Bacillus thuringiensis* Cry1A.105, *Bacillus thuringiensis* Cry2Ab2, vipcot, vip3Aa19, E,E-9,11-tetradecadienyl acetate, *Bacillus thuringiensis* modified Cray 3, R-octonol, indole-3-acetic acid, sorbitol octanoate, methyl eugenol, potassium silicate, ammonium nonaoate, cuelure, ammonium bicarbonate, black pepper oil, iperine, citronellol, glycerol monocaprylate, propylene glycol, lysophosphatidylethanolamines, corn gluten meal, dipotassium phosphate, sucrose octanoate esters, silver nitrate, formic acid, xanthine, verbenone, fish oil, kaolin, canola oil, potassium dihydrogen phosphate, maple lactone, anthrquinone, acetic acid, iron phosphate, polyoxin D zinc salt, dihydroazadirachtin, and mixtures thereof.

According to one embodiment, the at least one pesticidal active ingredient is a plant growth regulator. Suitable plant growth regulators include, but are not limited to, ancymidol, azoluron, chlorflurenol-methyl, flurprimidol, forchlorfenuron, indolylbutyric acid, mefluidide, 1-naphthylacetamide, 1-naphthylacetic acid, 2-naphthyloxyacetic acid (ester), paclobutrazol, thidiazuron, 3-CPA, 4-CPA, BAP, butifos, tribufos, butralin, chlorflurenol, clofencet, cyclanilide, daminozide, dicamba, dikegulac sodium, dimethipin, chlorfenethol, etacelasil, ethephon, ethychlozate, fenoprop, 2,4,5-TP, fluoridamid, flurprimidol, flutriafol, guazatin, imazalil, karetazan, kinetin, lactidichlor-ethyl, maleic hydrazide, naptalam, quinmerac, sintofen, tetcyclacis, triiodobenzoic acid, triapenthenol, triazethan, tribufos, trinexapac-ethyl, uniconazole, propham and gibberillic acid, gibberellins and combinations thereof.

As provided herein, an at least one additional component is water, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof.

According to one embodiment, the at least one additional component is one or more surfactant. Such a surfactant may be one or more of an ionic and a non-ionic surfactant. Such surfactants may be used as an emulsifier, dispersant, solubilizer, wetter, penetrant, protective colloid, or for other purposes. Suitable ionic surfactants for use with the pesticidal composition described herein may include anionic surfactants such as alkali, alkaline earth or ammonium salts of sulfonates, sulfates, phosphates, carboxylates, and mixtures thereof. Suitable sulfonates include, but are not limited to, alkylarylsulfonates, diphenylsulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Suitable sulfates include, but are not limited to, sulfates of fatty acids and oils, of ethoxylated alkylphenols, of alcohols, of ethoxylated alcohols, or of fatty acid esters. Suitable phosphates include, but are not limited to, phosphate esters. Suitable carboxylates include, but are not limited to, alkyl carboxylates, and carboxylated alcohol or alkylphenol ethoxylates. Suitable anionic surfactants include, but are not limited to, sulfates and sulfonates.

According to one embodiment, the at least one additional component is one or more nonionic surfactant. Suitable nonionic surfactants include, but are not limited to, alkoxylates, N-substituted fatty acid amides, amine oxides, esters, sugar-based surfactants, polymeric surfactants, and mixtures thereof. Suitable alkoxylates include, but are not limited to, compounds such as alcohols, alkylphenols, amines, amides, arylphenols, fatty acids or fatty acid esters which have been alkoxylated with from 1 to 50 molar equivalents of an alkoxylating agent such as, for example, ethylene oxide (EO), propylene oxide (PO), or a combination thereof.

According to another embodiment, the one or more nonionic surfactant is an alcohol initiated EO/PO block copolymer such as a butanol initiated EO/PO block copolymer, which may also be known as a polyalkylene glycol monobutyl ether, a poly(ethylene glycol-co-propylene glycol) monobutyl ether, or a propylene oxide ethylene oxide polymer monobutyl ether. According to one embodiment, the butanol initiated EO/PO block copolymer may have a degree of ethoxylation of from about 20 to about 30 and a degree of propoxylation of from about 20 to about 30. Suitable examples of EO/PO block copolymers include, but are not limited to, Toximul® 8320 available from Stepan (Northfield, Ill.), Termul® 5429 available from Huntsman International LLC (The Woodlands, Tex.), Tergitol™ XD available from Dow Chemical (Midland, Mich.), and Ethylan™ NS 500LQ available from AkzoNobel (Chicago, Ill.).

According to one embodiment, the surfactant is one or more quaternary ammonium surfactant. Suitable quaternary ammonium surfactants include ARQUAD 2C-75 (available from Akzo Nobel, Chicago, Ill.), quaternary ammonium chloride salts, cocodimethyl and dicocodimethylammonium chloride, and other coco-substituted quaternary ammonium salts. According to one embodiment, the surfactant is one or more alkyl, primary, secondary or tertiary amine. According to one embodiment, the surfactant is one or more amine with alkyl groups or a linear alkenyl groups with a carbon number of 8 to 20. According to one embodiment, the surfactant is derived from natural oil or fat. According to one embodiment, the surfactant, includes one or more an oxyalkylene groups. Suitable amines include, but are not limited to, any of the ARMEEN aliphatic amines (available from Akzo Nobel), mono-long-chain alkylamine, for example, bis(2-hydroxyethyl)cocoamine, bis(2-hydroxyethyl)-tallowamine, bis(2-hydroxyethyl)oleylamine, and bis(2-hydroxyethyl)laurylamine, polyoxyalkylenated long-chain alkylamine, for example, bis(polyoxyethylene($EOp=3$ to 30))cocoamine, bis(polyoxyethylene($EOp=3$ to 30))tallowamine, bis(polyoxyethylene(EOp 3 to 30))oleylamine, bis(polyoxyethylene ($EOp=3$ to 30))laurylamine, bis(polyoxyethylene($EOp=3$ to 30))palmstearylamine, bis(polyoxyethylene($EOp=3$ to 10)polyoxypropylene-($POp=3$ to 10)cocoamine, and bis (polyoxyethylene ($EOp=3$ to 10)polyoxypropylene ($POp=3$ to 10)tallowamine. In the compounds described above, EOp represents an average addition mole number of ethylene oxide, and POp represents an average addition mole number of propylene oxide.

According to one embodiment, the surfactant includes one or more chelating agent and one or more cation compound. Combinations of oxalic acid and citric acid may be utilized due to the combination's action as an effective permeabilizer without exhibiting toxicity on exposure. According to one embodiment, citric acid lowers oxalic acid toxicity and also functions as a permeabilizing agent.

According to one embodiment, the at least one additional component is at least one inert formulation ingredient Suitable inert formulation ingredients include, but are not limited to, dispersants, surfactants and wetting agents. Additional composition components may also include, for example, one or more ingredients, which may be dissolved or dispersed in the composition and may be selected from acaricides, algicides, antifeedants, avicides, bird repellents, chemosterilants, defoliants, desiccants, disinfectants, herbicide safeners, flow agents, insect attractants, insect repellents, mammal repellents, mating disrupters, molluscicides, nematicides, plant activators, plant growth regulators, rodenticides, semiochemicals, synergists, virucides, antifoam agents, antimicrobial agents, buffers, corrosion inhibitors, dispersing agents, dyes, fragrants, freezing point depressants, neutralizing agents, odorants, penetration aids, sequestering agents, spray drift control agents, spreading agents, stabilizers, sticking agents, viscosity-modifying additives, preservatives, plasticizers, hydrophobic barriers, UV protectants, water soluble solvents and mixtures thereof.

According to one embodiment, the at least one additional component is at least one flow agent. Suitable flow agents include, but are not limited to, clays such as kaolin, talc, diatomaceous earth and propylene glycol.

According to one embodiment, the at least one additional component is a component to aid in forming a film on the surface of a crop plant. Such a film forming component may include, but are not limited to, cellulose acetate, cellulose acetate-succinate, cellulose acetate phthalate, hydroxyethylcellulose, hydroxypropylcellulose, carboxymethylcellulose, carboxyethylcellulose, chitosan, methylcellulose, ethyl cellulose, propylcellulose, butylcellulose, alkylcelluloses, phthalate and acetate esters of cellulose, hypromellose, hypromellose acetate succinate, hypromellose phthalate, xanthan gum, guar gum, gellan gum, gum arabic, carageenan, alginic acid (and its salts), acacia, tragacanth, polyvinyl acetate, polyvinyl alcohol, polyvinylpyrolidone, polyvinylacetate phthalate, methacrylic-acrylic acid copolymer and its alkyl esters or ethers and combinations thereof.

According to one embodiment, the at least one additional component increases the adhesion of a particular component or composition to the target area (i.e., leaf). The adhesion component may aid in rain fastness. Suitable adhesion components include the film forming compounds provided herein, polyvinyl alcohol, polyvinylpyrolidone, or any combination thereof.

According to one embodiment, the at least one additional component increases the penetration of the pesticidal active ingredient. Suitable penetration components include, but are not limited to, oranosilicone-based surfactants.

According to one embodiment, the at least one additional component is a component that aids in drift control. Suitable drift control components include, but are not limited to, viscoelastic polymers.

According to one embodiment, the at least one additional component is a suitable base or pH control agent. According to a particular embodiment, the base is potassium hydroxide.

According to one embodiment, the at least one additional component is at least one permeabilizing agent. According to one embodiment, the at least one permeabilizing agent is at least one chelating agent. According to one embodiment, the at least one chelating agent is ethylenediaminetetraacetic acid (EDTA), diethylenetriaminepentaacetic acid (DTPA), (hydroxyethyl)ethylenediaminetriacetic acid (HEDTA), nitrilotriacetic acid (NTA), oxalic acid, citric acid, sugars, amino acids, organic diacids, diamines, alpha ketoacids, alphahydroxyacids, aminodiacids, amino tri-acids, amino tetra-acids, t-dol amines, organic polyacids (and their sodium, potassium, and ammonium salts), salts of maleic acid, malonic acid, tartaric acid, glycine, lactic acid, malic acid, succinic acid, dextrose, tris(hydroxymethyl)aminomethane, lactose, mannitol, glutaric acid, malic acid, succinic acid, glycerol, humic acid, fulvic acid, sorbic acid, sorbose, ethylene diamine, 1,2 diaminocyclohexane, trimethylenediamine, tetramethylenediamine, 1,2 diaminopropane, diethylenetriamine, triethylenetetramine, triaminodiethylamine, N-hydroxyethylethylenediamine, sodium polyphosphate, potassium polyphosphate, ammonium polyphosphate, sodium hexametaphosphate and mixtures thereof.

According to one embodiment, the at least one additional component is water conditioning agent. Suitable water conditioning agents include, but are not limited to, pH buffering agents.

According to one embodiment, the at least one additional is at least one component or chemical disclosed by Harris in U.S. Pat. No. 9,113,625 and Miles in U.S. Pat. No. 7,476,646, the contents of which are each herein incorporated by reference.

A tank mix pesticidal composition is also provided. The tank mix composition may be applied directly to a target plant or pest. The tank mix pesticidal composition is particularly suited for direct application to at least one crop plant, the surrounding soil, turf, seed, or a combination thereof. The tank mix pesticidal composition reduces or eliminates at least one or more fungus, bacteria, weed, insect or other pest.

According to one embodiment, the tank mix pesticidal composition includes at least one pesticidal active ingredient, at least one pesticidal active ingredient and at least one organic solvent. According to one embodiment, the tank mix pesticidal composition further includes water, spray oil, or a combination thereof.

The at least one organic solvent included in the tank mix pesticidal composition is any organic solvent as provided herein. Suitable organic solvents include, but are not limited to, propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, or any combination thereof. According to a particular embodiment, the at least one organic solvent included in the pesticidal composition is benzyl acetate. According to a particular embodiment, the at least one organic solvent included in the pesticidal composition is propylene carbonate. According to a particular embodiment, the at least one organic solvent included in the pesticidal composition is N-methylpyrrolidone. According to one embodiment, the at least one active ingredient in the tank mix pesticidal composition at least one pesticidal active ingredient as provided herein.

The tank mix pesticidal compositions may be formed by combining at least one organic solvent as provided herein, at least one pesticidal active ingredient, and optionally at least one of any variety of additional components as provided herein. According to a particular embodiment, the at least one organic solvent, pesticidal active ingredient, water, spray oil, and any optional additional components may be added to a tank to form a tank mix pesticidal composition. At least one de-foamer composition may be added to the pesticidal composition at the time of mixing.

According to a particular embodiment, a tank mix pesticidal composition is provided that includes from typically about 0.2% v/v to about 5% v/v of at least one pesticidal active ingredient. According to a particular embodiment, a tank mix pesticidal composition is provided that includes from typically about 0.2% v/v to about 2 v/v % of at least one organic solvent. According to a particular embodiment, a tank mix pesticidal composition is provided that includes from typically about 80% v/v to about 99% of a water, spray oil (e.g., phytobland or paraffinic oil), or a combination thereof.

The tank mix pesticidal compositions or as provided herein may be applied to plant leaves as foliar sprays, or to plant shoots, or to the surrounding soil or to seed. According to one embodiment, the tank mix pesticidal compositions as provided herein may be applied via a sprayer attached to a tank containing the pesticidal composition.

According to one embodiment, the tank mix pesticidal compositions as provided herein may be applied via an irrigation system (chemigation). According to one embodiment, the tank mix pesticidal compositions as provided herein may be applied as a drench treatment. According to one embodiment, the tank mix pesticidal compositions as provided herein may be applied as a wick system.

An adjuvant composition is also provided. The adjuvant compositions as provided herein may be utilized to improve the efficacy of at least one active ingredient such as a fungicide, bactericide, herbicide, insecticide, pesticide, or biopesticide. According to one embodiment, the at least one pesticidal active ingredient may be sufficient to reduce, halt, or eliminate growth of various target pests such as fungi, bacteria, insects, or weeds. According to one embodiment, the adjuvant compositions as provided herein may be utilized to improve the efficacy of at least one pesticidal active ingredient such that the pesticidal active ingredient is more efficacious against at least one resistant pest such as a fungi, bacteria, insect or weed compared to when the active ingredient is utilized alone.

According to one embodiment, the adjuvant compositions include at least on organic solvent as provided herein. According to a particular embodiment, the at least one organic solvent included in the adjuvant composition is benzyl acetate. According to a particular embodiment, the at least one organic solvent included in the pesticidal composition is propylene carbonate. According to a particular embodiment, the at least one organic solvent included in the pesticidal composition is N-methylpyrrolidone.

According to one embodiment, the adjuvant compositions as provided herein may further at least one additional component as provided herein. Particularly suitable additional components include, but are not limited to, water, citric acid, potassium hydroxide, cocodimethylamine, polyoxyethylene sorbitan monolaurate (commercially available as Tween™ 21), at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof.

According to one embodiment, the adjuvant composition includes typically at least from about 10% by volume (v/v) to about 98% by volume (v/v) of at least one organic solvent as provided herein. According to one embodiment, the adjuvant composition includes typically at least from about 20% by volume (v/v) of at least one organic solvent as provided herein. According to one embodiment, the adjuvant composition includes typically at least from about 30% by volume (v/v) of at least one organic solvent as provided herein. According to one embodiment, the adjuvant composition includes typically at least from about 40% by volume (v/v) of at least one organic solvent as provided herein. According to one embodiment, the adjuvant composition includes typically at least from about 50% by volume (v/v) of at least one organic solvent as provided herein. According to one embodiment, the adjuvant composition includes typically at least from about 60% by volume (v/v) of at least one organic solvent as provided herein. According to one embodiment, the adjuvant composition includes typically at least from about 70% by volume (v/v) of at least one organic solvent as provided herein. According to one embodiment, the adjuvant composition includes typically at least from about 75% by volume (v/v) of at least one organic solvent as provided herein. According to one embodiment, the adjuvant composition includes typically at least from about 80% by volume (v/v) of at least one organic solvent as provided herein.

According to one embodiment, the adjuvant composition includes typically at least from about 2% by volume (v/v) to about 90% by volume (v/v) of at least one additional component as provided herein. According to one embodiment, the adjuvant composition includes typically at least from about 5% by volume (v/v) of at least one additional component as provided herein. According to one embodiment, the adjuvant composition includes typically at least from about 10% by volume (v/v) of at least one additional component as provided herein. According to one embodiment, the adjuvant composition includes typically at least from about 15% by volume (v/v) of at least one additional component as provided herein. According to one embodiment, the adjuvant composition includes typically at least from about 20% by volume (v/v) of at least one additional component as provided herein. According to one embodiment, the adjuvant composition includes typically at least from about 25% by volume (v/v) of at least one additional component as provided herein. According to one embodiment, the adjuvant composition includes typically at least from about 35% by volume (v/v) of at least one additional component as provided herein. According to one embodiment, the adjuvant composition includes typically at least from about 45% by volume (v/v) of at least one additional component as provided herein. According to one embodiment, the adjuvant composition includes typically at least from about 55% by volume (v/v) of at least one additional component as provided herein. According to one embodiment, the adjuvant composition includes typically at least from about 65% by volume (v/v) of at least one additional component as provided herein. According to one embodiment, the adjuvant composition includes typically at least from about 75% by volume (v/v) of at least one additional component as provided herein. According to one embodiment, the adjuvant composition includes typically at least from about 85% by volume (v/v) of at least one additional component as provided herein.

According to a particular embodiment, the adjuvant composition typically includes from about 0.0% v/v to about 2.0% v/v water. According to a particular embodiment, the adjuvant composition typically includes about 0.4% v/v water. According to a particular embodiment, the adjuvant composition typically includes from about 0.0% v/v to about 2.0% v/v citric acid. According to a particular embodiment, the adjuvant composition typically includes about 0.2% v/v citric acid. According to a particular embodiment, the adjuvant composition typically includes from about 0.0% v/v to about 2.0% v/v potassium hydroxide. According to a particular embodiment, the adjuvant composition typically includes about 0.2% v/v potassium hydroxide. According to a particular embodiment, the adjuvant composition typically includes from about 0.0% v/v to about 2.0% v/v cocodimethylamine. According to a particular embodiment, the adjuvant composition typically includes about 0.2% v/v cocodimethylamine. According to a particular embodiment, the adjuvant composition typically includes from about 20% v/v to about 99% v/v of at least one organic solvent. According to a particular embodiment, the at least one organic solvent is benzyl acetate, propylene carbonate, N-methylpyrrolidone, or any combination thereof. According to a particular embodiment, the adjuvant composition typically includes about 74% v/v benzyl acetate. According to a particular embodiment, the adjuvant composition typically includes from about 10% v/v to about 70% v/v of at least on surfactant. According to one embodiment, the at least one surfactant is polyoxyethylene sorbitan monolaurate. According to a particular embodiment, the adjuvant composition typically includes about 25% v/v polyoxyethylene sorbitan monolaurate.

According to a particular embodiment, the organic solvent is applied at an effective rate of typically at least about 0.1 fluid ounces/acre. According to a particular embodiment, the organic solvent is applied at an effective rate of typically at least about 1 fluid ounces/acre. According to a particular embodiment, the organic solvent is applied at an effective rate of typically at least about 2 fluid ounces/acre. According to a particular embodiment, the organic solvent is applied at an effective rate of typically at least about 3 fluid ounces/acre. According to a particular embodiment, the organic solvent is applied at an effective rate of typically at least about 4 fluid ounces/acre. According to a particular embodiment, the organic solvent is applied at an effective rate of typically at least about 5 fluid ounces/acre. According to a particular embodiment, the organic solvent is applied at an effective rate of typically at least about 6 fluid ounces/acre. According to a particular embodiment, the organic solvent is applied at an effective rate of typically at least about 7 fluid ounces/acre. According to a particular embodiment, the organic solvent is applied at an effective rate of typically at least about 8 fluid ounces/acre. According to a particular embodiment, the organic solvent is applied at an effective rate of typically at least about 9 fluid ounces/acre. According to a particular embodiment, the organic solvent is applied at an effective rate of typically at least about 10 fluid ounces/acre. According to a particular embodiment, the organic solvent is applied at an effective rate of typically at least about 11 fluid ounces/acre. According to a particular embodiment, the organic solvent is applied at an effective rate of typically at least about 12 fluid ounces/acre. According to a particular embodiment, the organic solvent is applied at an effective rate of typically at least about 13 fluid ounces/acre. According to a particular embodiment, the organic solvent is applied at an effective rate of typically at least about 14 fluid ounces/acre. According to a particular embodiment, the organic solvent is applied at an effective rate of typically less than about 15 fluid ounces/acre.

According to one aspect, a plant is provided that includes a pesticidal composition, adjuvant composition, or a tank mix pesticidal composition on a surface thereof.

According to one aspect, a kit is provided. The kit includes a container that includes an adjuvant composition or pesticidal composition as provided herein. The kit may optionally include instructions for use.

A method of producing an adjuvant composition for use in combination with at least one pesticidal active ingredient is provided. The method includes the step of introducing at least one organic solvent to a container. The at least one organic solvent includes propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, or any combination thereof. The method optionally includes the step of introducing at least one additional component to the container. The at least one additional component includes water, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof. The method optionally includes the step of attaching at least one set of instructions to the container.

The at least one organic solvent is introduced to the container in an amount such that entire contents of the container may be added directly to a spray tank containing at least one pesticidal active ingredient. According to a particular embodiment, at least one organic solvent is benzyl acetate. According to one embodiment, the adjuvant composition increases the efficacy of the at least one pesticidal active ingredient by at least about 25% compared to the at least one pesticidal active ingredient alone. According to one embodiment, the at least one pesticidal active ingredient is a fungicide, bactericide, herbicide, insecticide, pesticide, plant growth regulator, or biopesticide.

According to one embodiment, the adjuvant composition is added or mixed with the at least one active ingredient and water or spray oil in a tank at the time of spraying. According to one embodiment, limited amounts of the adjuvant composition are sufficient to increase the efficacy of the active ingredient by reducing the potential for phytotoxicity and leaving a portion of the active ingredient in solid form for residual activity.

A method of preparing a pesticidal composition is also provided. The method includes the steps of combining, within a container, at least one organic solvent as provided herein, at least one pesticidal active ingredient as provided herein, and, optionally, or more additional components as provided herein.

A method of enhancing the efficacy of a pesticidal active ingredient is provided. The method includes the step of introducing at least one adjuvant composition to at least one pesticidal active ingredient. The at least one adjuvant composition includes at least one organic solvent selected from the group consisting of propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, or any combination thereof. According to one embodiment, the efficacy of the active ingredient is increased by at least 25% compared to application of the pesticidal active ingredient without the adjuvant composition. According to one embodiment, the at least one active ingredient is a fungicide, bactericide, herbicide, insecticide, pesticide, or biopesticide. According to one embodiment, the organic solvent is benzyl acetate.

A method of improving the quality of at least one target plant is provided. The target plant may be a agronomic plant or horticultural plant. The method includes the step of applying a pesticidal composition to the surface of the at least one plant, the surrounding soil, turf, seed, or a combination thereof. The pesticidal composition that is applied includes at least one pesticidal active ingredient and at least one organic solvent. The at least one organic solvent may be propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, or any combination thereof. The method improves the quality of at least one crop by reducing or eliminating at least one or more fungus, bacteria, weed, insect or other pest thereby reducing such pressures and improving the quality of the crop. The at least one active ingredient utilized in the method may be a fungicide, bactericide, herbicide, insecticide, pesticide, or biopesticide. According to a particular embodiment, the organic solvent is benzyl acetate.

A method of increasing yield of a crop is provided. The method includes the step of applying a pesticidal composition to the surface of the at least one crop plant, the surrounding soil, turf, seed, or a combination thereof. The pesticidal composition that is applied includes at least one pesticidal active ingredient and at least one organic solvent. The at least one organic solvent may be propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, or any combination thereof. The method reduces or eliminates at least one or more fungus, bacteria, weed, insect or other pest thereby increasing crop yield. The at least one active ingredient utilized in the method may be a fungicide, bactericide, herbicide, insecticide, pesticide, or biopesticide. According to a particular embodiment, the organic solvent is benzyl acetate.

A method of reducing post blossom fruit drop is provided. The method includes the step of applying a pesticidal composition to the surface of the at least one crop plant, the surrounding soil, turf, seed, or a combination thereof. The pesticidal composition that is applied includes at least one pesticidal active ingredient and at least one organic solvent. The at least one organic solvent may be propylene carbonate, N-methylpyrrolidone, benzyl acetate, benzyl butyrate, benzyl propionate, diethyl malonate, 3-methoxy-3-methyl-1-butanol, dimethyl benzyl carbinol acetate, phenyl ethyl alcohol, terpinyl acetate, benzyl benzoate, methyl sailcylate, hexyl acetate, ethyl acetate, phenoxy ethyl iso-butyrate, terpineol, geranyl acetate, linalyl acetate, ethyl 2-methyl butyrate, propylene glycol diacetate, dipropylene glycol monomethyl ether, or any combination thereof. The method reduces post blossom fruit drop by reducing or eliminating at least one or more fungus, bacteria, weed, insect or other pest. The at least one active ingredient utilized in the method may be a fungicide, bactericide, herbicide, insecticide, pesticide, or biopesticide. According to a particular embodiment, the organic solvent is benzyl acetate.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Example 1

Throughout the Examples provided herein, the designation "ADJ1" refers to benzyl acetate and the designation "ADJ2" refers to alkylene carbonate.

Petri dish tests (i.e., zone of inhibition tests) were conducted which demonstrated that formulations containing the adjuvant compositions ADJ1 or ADJ2 in addition to azoxystrobin (Quadris®) have at least greater than 25% reduction in radial growth on a sensitive strain of *Didymella* sp. (gummy stem rot) compared to treatment with azoxystrobin (Quadris®) alone. The results are presented in Table 1 below.

TABLE 1

| Quadris® rate (fluid oz/Acre) | Quadris® rate | Additive | Adjuvant Rate (fluid oz/Acre) | 24 hours, cm | 48 hrs, cm | 72 hrs, cm |
|---|---|---|---|---|---|---|
| 11 | .5x | ADJ1 | 4 | 15.9 | 42 | 47.1 |
| 8 | .37x | ADJ1 | 4 | 16.6 | 43.3 | 49.5 |
| 5.5 | .25x | ADJ1 | 4 | 18.1 | 49 | 59.9 |
| 2.6 | .12x | ADJ1 | 4 | 17.9 | 58 | 70.9 |
| 11 | .5x | ADJ2 | 4 | 14.6 | 49.1 | 57.8 |
| 8 | .37x | ADJ2 | 4 | 20.3 | 45.4 | 53.5 |
| 5.5 | .25x | ADJ2 | 4 | 21.9 | 48.5 | 61.3 |
| 2.6 | .12x | ADJ2 | 4 | 22.4 | 46.5 | 59.6 |
| 22 | 1x | none | 0 | 24.9 | 54.3 | 72.3 |
| 16.5 | .75x | none | 0 | 26.6 | 56.5 | 74.1 |
| 11 | .5x | none | 0 | 24.8 | 59.9 | 75.4 |
| 5.5 | .25x | none | 0 | 26 | 63.5 | 85.5 |
| 0 | 0x | Untreated/control | 0 | 26.9 | 74.1 | 88 |

Example 2

Petri dish tests (i.e., zone of inhibition tests) were conducted to compare the efficacy of azoxystrobin against both sensitive/susceptible and resistant strains of *Didymella* sp. (gummy stem rot). To treat the susceptible strain, the equivalent of 2 oz/acre of ADJ1 was shown to give comparable control to azoxystrobin alone (below effective rate for ADJ1). To treat the resistant strain, adding 2 oz of ADJ1 was shown to give twice as much growth reduction compared to azoxystrobin alone at equivalent rates. Control of resistant strain was shown to be comparable to azoxystrobin on susceptible strains. ADJ1 alone showed some efficacy but not at a commercial level control. A calcium complex did not add to growth reduction. The results are presented in Tables 2 and 3.

TABLE 2

| Adjuvant Rate (fl. oz/acre) | Quadris ® Rate (fluid oz/acre) | Name | 18 hours, cm | 24 hours, cm | 36 hours, cm | 48 hours, cm |
|---|---|---|---|---|---|---|
| 0 | 0 | Untreated/Control - sensitive | 23.9 | 37.2 | 52.6 | 64.2 |
| 8 | 0 | Calcium Complex + ADJ1 | 19.6 | 25.1 | 42.9 | 51.9 |
| 0 | 14.0 | Quadris ® 1X | 10.1 | 11.8 | 25.8 | 31.9 |
| 0 | 12.75 | Quadris ® 0.75X | 10.9 | 13.6 | 24.1 | 27.2 |
| 0 | 7.0 | Quadris ® 0.5X | 10.4 | 13.9 | 16.6 | 25 |
| 0 | 3.5 | Quadris ® 0.25X | 17.6 | 13.5 | 20.5 | 20.6 |
| 8 | 0 | ADJ1 1X | 15.7 | 21.3 | 40.6 | 50.1 |
| 6 | 0 | ADJ1 0.75X | 15.7 | 26.1 | 38.8 | 48.1 |
| 4 | 0 | ADJ1 0.5X | 17 | 23.7 | 32.3 | 46 |
| 2 | 0 | ADJ 0.25X | 19.9 | 24.9 | 39.3 | 47.9 |
| 4 | 14 | ADJ1 0.5X + Quadris ® 1X | 8.4 | 13.9 | 19.1 | 24.6 |
| 4 | 12.75 | ADJ1 0.5X + Quadris ® 0.75X | 9 | 12.4 | 19.5 | 28.2 |
| 4 | 7.0 | ADJ1 0.5X + Quadris ® 0.5X | 14 | 16.1 | 25.5 | 31 |
| 4 | 3.5 | ADJ1 0.5X + Quadris ® 0.25X | 14.5 | 17.5 | 24.1 | 27.6 |

TABLE 3

| Adjuvant Rate (fl. oz/acre) | Quadris ® Rate (fluid oz/acre) | Name | 18 hours, cm | 24 hours, cm | 36 hours, cm, cm | 48 hours, cm |
|---|---|---|---|---|---|---|
| 0 | 0 | Untreated - resistant | 29.5 | 38.4 | 51.6 | 66.4 |
| 4 | 0 | Calcium Complex + ADJ1 | 19.9 | 24.9 | 40.3 | 50.1 |
| 0 | 14.0 | Quadris ® 1X | 22.6 | 32 | 44.3 | 57.7 |
| 0 | 12.75 | Quadris ® 0.75X | 29.7 | 37.5 | 49.4 | 62.5 |
| 0 | 7.0 | Quadris ® 0.5X | 30.1 | 37.4 | 50.9 | 64.2 |
| 0 | 3.5 | Quadris ® 0.25X | 30 | 38.4 | 49.6 | 64.5 |
| 8 | 0 | ADJ1 1X | 16.7 | 10.9 | 35.1 | 44.4 |
| 6 | 0 | ADJ1 0.75X | 18.9 | 23.4 | 35.4 | 45.9 |
| 4 | 0 | ADJ1 0.5X | 22.6 | 28.5 | 44.3 | 53.9 |
| 4 | 0 | ADJ1 0.25X | 20.6 | 30.2 | 42 | 51.2 |
| 4 | 14 | ADJ1 0.5X + Quadris ® 1X | 13.5 | 9.7 | 21.9 | 24.9 |
| 4 | 12.75 | ADJ1 0.5X + Quadris ® 0.75X | 13 | 12 | 19.6 | 28.2 |
| 4 | 7.0 | ADJ1 0.5X + Quadris ® 0.5X | 18.5 | 17.6 | 28.4 | 35 |
| 4 | 3.5 | ADJ1 0.5X + Q Quadris ® 0.25X | 18.6 | 19.7 | 31.1 | 39.7 |

Example 3

Petri dish tests (i.e., zone of inhibition tests) were conducted to compare four rates of three adjuvant compositions (ADJ1, AJD2, and ADJ3 (N-methylpyrrolidone)) on sensitive and resistant strains of *Didymella* at a fixed treatment rate with azoxystrobin. All three adjuvant compositions were shown to provide excellent control of resistant strain at the lowest azoxystrobin label rates. The results are presented in Tables 4 (sensitive strain) and 5 (resistant strain) below.

TABLE 4

| azoxystrobin Rate (fl. oz/acre) | Additive | Additive Rate | 12 hours, cm | 24 hours, cm | 36 hours, cm |
|---|---|---|---|---|---|
| Untreated Sensitive | 0 | 0 | 24.9 | 41.4 | 60.5 |
| 22 | 0 | 0 | 15.8 | 22.9 | 31.9 |
| 16 | 0 | 0 | 13.4 | 20 | 28 |
| 11 | 0 | 0 | 12.5 | 16.9 | 23.6 |
| 5.5 | 0 | 0 | 15.3 | 24.9 | 34.3 |
| 7 | ADJ1 | 8 | 11.3 | 16.8 | 21 |
| 7 | ADJ1 | 4 | 15.6 | 22 | 28.9 |
| 7 | ADJ1 | 2 | 12.8 | 16 | 21 |
| 7 | ADJ1 | 1 | 13.8 | 19.5 | 25 |
| 0 | ADJ1 | 0 | 24 | 41.1 | 54 |
| 7 | ADJ2 | 8 | 15.1 | 21.8 | 27.5 |
| 7 | ADJ2 | 4 | 14.6 | 21.5 | 30 |
| 7 | ADJ2 | 2 | 15.5 | 24 | 31.1 |
| 7 | ADJ2 | 1 | 17.4 | 25.3 | 32 |
| 0 | ADJ2 | 0 | 24.3 | 39.6 | 53.6 |
| 7 | ADJ3 | 8 | 15 | 21.1 | 27.6 |
| 7 | ADJ3 | 4 | 14.9 | 21.8 | 29.6 |
| 7 | ADJ3 | 2 | 17.3 | 24.9 | 30.1 |
| 7 | ADJ3 | 1 | 17.1 | 25.1 | 32.6 |
| 0 | ADJ3 | 0 | 22.8 | 41 | 54.1 |

TABLE 5

| azoxystrobin Rate (fl. oz/acre) | Additive | Additive Rate | 12 hours, cm | 24 hours, cm | 36 hours, cm |
|---|---|---|---|---|---|
| Untreated Resistant | 0 | 0 | 31 | 49 | 70 |
| 22 | 0 | 0 | 22 | 28 | 35 |
| 16 | 0 | 0 | 29 | 47 | 68 |
| 11 | 0 | 0 | 30 | 48 | 70 |
| 5.5 | 0 | 0 | 31 | 48 | 70 |
| 7 | ADJ1 | 8 | 15 | 22 | 29 |
| 7 | ADJ1 | 4 | 18 | 25 | 35 |
| 7 | ADJ1 | 2 | 17 | 23 | 35 |
| 7 | ADJ1 | 1 | 19 | 27 | 41 |
| 0 | ADJ1 | 0 | 25 | 30 | 56 |
| 7 | ADJ2 | 8 | 19 | 22 | 29 |
| 7 | ADJ2 | 4 | 19 | 26 | 39 |
| 7 | ADJ2 | 2 | 21 | 31 | 45 |
| 7 | ADJ2 | 1 | 20 | 29 | 41 |
| 0 | ADJ2 | 0 | 26 | 38 | 58 |
| 7 | ADJ3 | 8 | 12 | 27 | 35 |
| 7 | ADJ3 | 4 | 16 | 27 | 40 |
| 7 | ADJ3 | 2 | 17 | 27 | 45 |
| 7 | ADJ3 | 1 | 19 | 24 | 41 |
| 0 | ADJ3 | 0 | 27 | 39 | 60 |

Example 4

Watermelon *Didamella* (Gummy Stem Rot) Field Test

Watermelon plants were inoculated with an azoxystrobin resistant strain of *Didymella*. The watermelon plants were then treated with: (a) azoxystrobin alone; (b) azoxystrobin plus ADJ1; (c) azoxystrobin plus ADJ2; (d) azoxystrobin plus a typical commercial adjuvant (commercially available as Ad-Spray™); and (e) azoxystrobin plus chlorothalonil and commercial adjuvant (commercially available as Ad-Spray™). Disease severity ratings were taken and illustrated improved disease control of resistant strain with ADJ1 and ADJ2 compared to treatment with azoxystrobin alone, azoxystrobin plus commercial adjuvant, and azoxystrobin plus chlorothalonil and commercial adjuvant, especially at lower rates of azoxystrobin. Severity rating were based on multiple counts of active fungal infection sites on the leaves of the plants. The results are summarized in Table 6 below.

TABLE 6

| Treatment | azoxystrobin application rate | Adjuvant | Adjuvant Rate (fl. oz/acre) | One Week Rating | Two Week Rating | Third Week Rating | Fourth Week Rating |
|---|---|---|---|---|---|---|---|
| Untreated | 0 | None | none | 11.8 | 18.4 | 42.6 | 64.9 |
| azoxystrobin | 22 | None | 6 | 1.1 | 0.2 | 4.8 | 16.3 |
| azoxystrobin | 11 | None | 6 | 13.3 | 16.7 | 42 | 65.7 |
| azoxystrobin | 5.5 | None | 6 | 9.2 | 16.9 | 63.3 | 82.8 |
| azoxystrobin | 22 | ADJ1 | 6 | 0.5 | 0.6 | 5.1 | 8.4 |
| azoxystrobin | 11 | ADJ1 | 6 | 0.6 | 0 | 0 | 3.2 |
| azoxystrobin | 5.5 | ADJ1 | 6 | 4.4 | 1.5 | 10.9 | 18.7 |
| azoxystrobin | 22 | Ad-Spray™ | 4 | 0.5 | 0.6 | 11 | 9.5 |
| azoxystrobin | 11 | Ad-Spray™ | 4 | 6.4 | 0 | 10.2 | 23.6 |
| azoxystrobin | 5.5 | Ad-Spray™ | 4 | 9.3 | 3.4 | 39 | 60.6 |
| azoxystrobin | 22 | ADJ2 | 6 | 3.9 | 1.2 | 1.5 | 5.1 |
| azoxystrobin | 11 | ADJ2 | 6 | 9.1 | 0.2 | 2.4 | 9 |
| azoxystrobin | 5.5 | ADJ2 | 6 | 7.7 | 0.4 | 11.5 | 20.6 |
| azoxystrobin plus chlorothal | 22 | Ad-Spray™ | 4 | 0 | 0 | 48 | 64.6 |
| azoxystrobin plus chlorothal | 11 | Ad-Spray™ | 4 | 1 | 0 | 4 | 42.9 |
| azoxystrobin plus chlorothal | 5.5 | Ad-Spray™ | 4 | 8.7 | 0 | 10.1 | 58.8 |

Example 5

Watermelon *Didymella* (Gummy Stem Rot) Field Test

Watermelon plants were grown in normal field conditions subject to infection by natural strains of *Didymella*. The watermelons where then treated with: (a) azoxystrobin alone; (b) ADJ1 alone; (c) azoxystrobin plus ADJ2; (d) azoxystrobin plus a typical commercial adjuvant (commercially available as Ad-Spray™); and (e) azoxystrobin plus chlorothalonil and commercial adjuvant. Disease severity ratings were taken and illustrated improved disease control of natural strains with ADJ1 compared to treatment with azoxystrobin alone or azoxystrobin plus commercial adjuvant, and equivalent control to azoxystrobin plus chlorothalonil and commercial adjuvant. Some disease reduction was observed with ADJ1 only. The results are summarized in Table 7 below.

Example 6

Soybean Cercospora (Frog Eye Leaf Spot) Field Test

Soybean plants were grown in normal field conditions subject to infection by natural strains of Cercospora (known to be resistant to azoxystrobin) then treated with: (a) azoxystrobin alone; (b) azoxystrobin plus ADJ1; (c) azoxystrobin plus ADJ2; (d) azoxystrobin plus a typical commercial adjuvant (commercially available as Preference®). Disease severity ratings were taken and illustrated improved disease control with ADJ1 and ADJ2 compared to treatment with azoxystrobin alone or azoxystrobin plus commercial adjuvant. Duncan Multiple Range treatment of the data (indicated by "a," "b," "c,", etc.) confirmed statistically valid different between the treatment results. The results are summarized in Table 8 below.

TABLE 7

| Treatment | azoxystrobin Application Rate (fl. oz/acre) | Adjuvant | Adjuvant Rate (fl. oz/acre) | One Week Rating | Two Week Rating | Third Week Rating | Fourth Week Rating |
|---|---|---|---|---|---|---|---|
| Untreated | 0 | none | none | 0 | 14.4 | 96.1 | 100 |
| azoxystrobin | 11 | none | 6 | 1.1 | 0 | 49.5 | 76.8 |
| azoxystrobin | 5.5 | none | 6 | 2.1 | 6.6 | 59.4 | 80.8 |
| azoxystrobin | 11 | Ad-Spray™ | 4 | 0 | 0 | 12.1 | 30.9 |
| azoxystrobin | 5.5 | Ad-Spray™ | 4 | 0.9 | 1.5 | 54.4 | 76.4 |
| Adjuvant Only | 0 | ADJ1 | 6 | 1.1 | 8 | 38.9 | 48.7 |
| azoxystrobin | 11 | ADJ1 | 6 | 0.2 | 0.2 | 0.9 | 3.4 |
| azoxystrobin | 5.5 | ADJ1 | 6 | 6.8 | 2.2 | 17.8 | 25.1 |
| azoxystrobin plus chlorothalonil | 11 | Ad-Spray™ | 4 | 0 | 0 | 0.6 | 5.9 |

TABLE 8

| | Severity Ratings | | | | | | | | | | | |
|---|---|---|---|---|---|---|---|---|---|---|---|---|
| | August 31/Upper leaf | | September 7/higher leaf | | September 7/bottom leaf | | September 7/middle leaf | | September 13/bottom leaf | | September 20/higher leaf | |
| Untreated | 13.5 | a | 21.5 | a | 69.3 | | 31.6 | a | 29 | a | 17.3 | a |
| Azoxystrobin 0.5x | 10.3 | ab | 16.3 | a | 35.5 | b | 3.2 | c | 18 | b | 11.3 | b |
| Azoxystrobin 0.5x + ADJ1 | 1 | c | 4 | b | 38.8 | b | 1.9 | c | 5.3 | d | 3.3 | c |
| Azoxystrobin 0.5x + ADJ2 | 1.5 | c | 2.3 | b | 36 | b | 1.7 | c | 1.5 | d | 1 | c |
| Azoxystrobin 0.5x + Commercial Adjuvant | 8 | b | 6.5 | b | 40.3 | b | 3.4 | c | 12 | c | 9.3 | b |

Example 7

Corn Maydis (Southern Corn Blight) and Southern Corn Rust Field Test

Corn plants were grown in normal field conditions subject to infection by natural strains known to be resistant to azoxystrobin then treated with: (a) azoxystrobin plus picoxystrobin alone; (b) azoxystrobin plus pixocystrobin plus ADJ1; (c) azoxystrobin plus ADJ2; and (d) azoxystrobin plus picoxystrobin plus a typical commercial adjuvant (commercially available as Preference®). Disease severity ratings were taken and illustrated improved disease control with ADJ1 and ADJ2 compared to treatment with azoxystrobin alone or azoxystrobin plus commercial adjuvant. Duncan Multiple Range treatment of the data confirms statistically valid different between the treatment results (indicated by "a," "b," "c,", etc.) in Table 9 below.

TABLE 9

| Days after Treatment (DAT) | Application Rate (fl. oz/acre) | Severity Rating | | | | | | | | | | |
|---|---|---|---|---|---|---|---|---|---|---|---|---|
| | | 21 | | 22 | | 23 | | 24 | | 25 | | 26 |
| Untreated | none | 40.2 | a | 100 | a | 100 | a | 84.8 | a | 55.2 | a | 100 |
| Azoxystrobin + Picoxystrobin 0.5x | 7 | 0.2 | b | 93.7 | a | 70.6 | b | 79.4 | a | 17.6 | b | 69.8 |
| Azoxystrobin + Picoxystrobin 0.5x ADJ1 | 7 6 | 0.2 | b | 54.6 | c | 24 | c | 13 | c | 1.4 | c | 3.5 |
| Azoxystrobin + Picoxystrobin 0.5x ADJ2 | 7 6 | 0 | b | 62.4 | bc | 25.3 | c | 10.5 | c | 1.5 | c | 3.1 |
| Azoxystrobin + Picoxystrobin 0.5x Commercial Adjuvant | 7 6 | 0.2 | b | 98.5 | a | 74.7 | b | 59 | ab | 19.6 | b | 55.3 |

| Days after Treatment (DAT) | Application Rate (fl. oz/acre) | Severity Rating | | | | | | | | | | |
|---|---|---|---|---|---|---|---|---|---|---|---|---|
| | | 27 | | 28 | | 29 | | 30 | | 31 | | |
| Untreated | none | a | 100 | a | 91.2 | a | 76.4 | a | 70.8 | a | 67.2 | a |
| Azoxystrobin + Picoxystrobin 0.5x | 7 | b | 80.9 | b | 66.4 | b | 66.6 | a | 50.7 | ab | 25.4 | b |
| Azoxystrobin + Picoxystrobin 0.5x ADJ1 | 7 6 | e | 4.5 | d | 6.1 | d | 5.6 | c | 2.8 | c | 3.7 | d |
| Azoxystrobin + Picoxystrobin 0.5x ADJ2 | 7 6 | e | 2.4 | d | 3.4 | d | 5.1 | c | 2.3 | c | 3.6 | d |
| Azoxystrobin + Picoxystrobin 0.5x Commercial Adjuvant | 7 6 | c | 47.2 | c | 45.7 | c | 37.4 | b | 39.9 | ab | 27.1 | b |

Example 8

Greenhouse Phytotoxicity (Crop Injury) Test

To evaluate the potential for ADJ1 to increase the risk for crop injury, watermelon, radish, and tomato plants were grown in the greenhouse and treated with a rate of azoxystrobin equal to four times the maximum label rate at weekly intervals. The data in tables 10, 11 and 12 confirm that azoxystrobin at 4× rate plus ADJ1 presented significantly less crop injury than azoxystrobin at 4× plus typical commercial adjuvant (commercially available as Preference®). Duncan Multiple Range treatment of the data (indicated by "a," "b," "c,", etc.) confirmed statistically valid different between the treatment results.

TABLE 10

| | Azoxystrobin Application Rate (fl. oz/acre) | Adjuvant Rate (fl. oz/acre) | Severity Rating | | Severity Rating | | Severity Rating | |
|---|---|---|---|---|---|---|---|---|
| Untreated-Watermelon | none | none | 0 | d | 0 | e | 0 | c |
| azoxystrobin 4× + ADJ1 | 56 | 24 | 3 | cd | 2.8 | e | 1.3 | c |
| azoxystrobin 4× + Commercial Adjuvant | 56 | 24 | 15.8 | b | 23.8 | b | 38.8 | b |

TABLE 11

| | Azoxystrobin Application Rate (fl. oz/acre) | Adjuvant Rate (fl. oz/acre) | Severity Rating | | Severity Rating | | Severity Rating | |
|---|---|---|---|---|---|---|---|---|
| Untreated-Radish | none | none | 0 | d | 0 | e | 0 | c |
| azoxystrobin 4× + ADJ1 | 56 | 24 | 2.3 | cd | 9.5 | d | 2.5 | c |
| azoxystrobin 4× + Commercial Adjuvant | 56 | 24 | 20.8 | a | 32.8 | a | 37.5 | b |

TABLE 12

| | Azoxystrobin Application Rate (fl. oz/acre) | Adjuvant Rate (fl. oz/acre) | Severity Rating | | Severity Rating | | Severity Rating | |
|---|---|---|---|---|---|---|---|---|
| Untreated-Tomato | none | none | 0 | d | 0 | e | 0 | c |
| azoxystrobin 4× + ADJ1 | 56 | 24 | 1.5 | cd | 2.8 | e | 6 | c |
| azoxystrobin 4× + Commercial Adjuvant | 56 | 24 | 16.8 | b | 20 | c | 10.5 | c |

Example 9

Citrus Post Bloom Fruit Drop

Efficacy of azoxystrobin, with or without ADJ1 or alternate commercial adjuvant (Activator 90) was tested against post bloom fruit drop causal agent, Colletotrichum acutatum, on Valencia oranges grown in a commercial orchard in Lake Wales, Fla. The azoxystrobin utilized was Abound® which is commercially available from Syngenta. Trees were spaced 12.5 feet apart on 25 feet wide beds and treated with foliar sprays with a single D6 nozzle on a handboom at a volume of 100 GPA weekly for four weeks. Colletotrichum-infected flowers were counted weekly. The trees treated with the higher rate of the combination of azoxystrobin and ADJ1 had the fewest infected flowers. Infected flower counts were significantly highest on the untreated orange trees but lowest for trees treated with the high rate of azoxystrobin with ADJ1. The results are summarized in Table 13.

TABLE 13

| | Number of Infected Flowers | | | | | |
|---|---|---|---|---|---|---|
| Days after treatment (DAT) | 0 | 7 | 15 | 20 | 27 | 36 |
| Untreated | 33 | 33.4 | 30.8 | 30.4 | 29.7 | 22.4 |
| azoxystrobin (Abound ®) 15.5 fl. oz plus adjuvant (Activator 90) | 26.6 | 27.5 | 11.1 | 8.3 | 5.9 | 4.5 |
| azoxystrobin (Abound ®) 15.5 fl. oz plus ADJ1 | 29.6 | 29.1 | 7.5 | 3.1 | 2.1 | 1.5 |

Example 10

Wheat Stripe Rust Control and Yield

Wheat was grown in normal field conditions subject to infection by natural strains known to be resistant to tebuconazole (1-(4-Chlorophenyl)-4,4-dimethyl-3-(1H-1,2,4-triazol-1-ylmethyl)-3-pentanol). The wheat was treated with: (a) tebuconazole (commercially available as Folicur®) plus commercial adjuvant ((commercially available as Preference®); (b) tebuconazole plus ADJ1; (c) a pre-formulated adjuvant composition of tebuconazole plus ADJ1. Disease severity ratings were taken and illustrated improved disease control with ADJ1 as well as ADJ1 pre-formulated with tebuconazole compared to treatment with tebuconazole plus commercial adjuvant. Duncan Multiple Range (DMR) treatment of the data (indicated by "a," "b," "c,", etc.) confirms statistically valid difference between the treatment results. To assess the effect on yield, the wheat was harvested and weighed. The results are summarized in the Tables 14 and 15 below.

TABLE 14

| | | 21 Days After Treatment | | 28 Days After Treatment | | 35 Days After Treatment | |
|---|---|---|---|---|---|---|---|
| | Application | | | | | | |
| Treatment | Rate (fl. oz/rate) | Severity Rating | Statistical Group | Severity Rating | DMR | Severity Rating | DMR |
| 1 Untreated | none | 29.7 | a | 49 | a | 64.3 | a |
| 2 Tebuconazole non-ionic surfactant | 2 4 | 10.2 | b | 20.3 | b | 33.2 | b |
| 3 Tebuconazole ADJ1 | 2 6 | 1.2 | c | 3.3 | c | 10.9 | c |
| 4 Tebuconazole plus ADJ1 (pre-formulated) | 2 | 0.4 | c | 2.2 | c | 8.7 | c |

TABLE 15

| Treatment | Yield Pounds | DMR Statistical Group | Yield Bushels | DMR Statistical Group | Percent Improvement vs NIS |
|---|---|---|---|---|---|
| 1 Untreated | 6.4 | c | 25.1 | c | |
| 2 Tebuconazole plus non-ionic surfactant | 12.55 | b | 49.2 | b | |
| 3 Tebuconazole plus ADJ1 | 14.78 | ab | 57.9 | ab | 18% |
| 4 Tebuconazole plus ADJ1 (pre-formulated) | 15.98 | a | 62.6 | a | 27% |

Example 11

Peanuts Sclerotenia Control

Peanuts were grown in the field using typical pesticidal practices and treated with Provost® Opti (commercially available) which is a mixture of tebuconazole and prothioconazole. The addition of ADJ1 statistically reduced the presence of Sclerotenia, generally referred to as White Mold which is a significant disease in peanuts compared to Provost combined with a commercially available adjuvant (commercially available as Induce®). Duncan Multiple Range (DMR) treatment of the data (indicated by "a," "b," "c,", etc.) confirms statistically valid difference between the treatment results. The data is presented in Table 16 below.

TABLE 16

| Treatment No. | Treatment Name | Application Rate (fl. oz/acre) | Severity Rating | Statistical Group |
|---|---|---|---|---|
| 1 | Untreated | none | 18.13 | a |
| 2 | Provost ® Opti ADJ1 | 8 6 | 4.37 | c |
| 3 | Provost ® Opti ADJ1 | 8 4 | 6.77 | bc |

TABLE 16-continued

| Treatment No. | Treatment Name | Application Rate (fl. oz/acre) | Severity Rating | Statistical Group |
|---|---|---|---|---|
| 4 | Provost ® Opti ADJ1 | 8 2 | 9.72 | ab |
| 5 | Provost ® Opti Induce ® | 8 6 | 12.33 | ab |

Example 12

Peanut Late Leaf Spot Control

Peanuts were grown in the field using typical pesticidal practices and treated with Priaxor which is a mixture of Pyraclostrobin and fluxapyroxad. The addition of ADJ1 statistically reduced the presence of Cercosporidium, commonly called Late Leaf Spot, a significant disease in peanuts. Duncan Multiple Range (DMR) treatment of the data (indicated by "a," "b," "c,", etc.) confirms statistically valid difference between the treatment results (at 90%). The data is presented in Table 17 below.

TABLE 17

| Treatment Number | Fungicide | Application Rate (fl. oz/acre) | Severity Rating | Statistical Group |
|---|---|---|---|---|
| 1 | Untreated | none | 360.758 | a |
| 2 | Priaxor ADJ1 | 6 6 | 241.830 | d |
| 3 | Priaxor ADJ1 | 6 4 | 247.484 | cd |
| 4 | Priaxor ADJ1 | 6 2 | 239.317 | d |
| 5 | Priaxor Induce | 6 6 | 268.748 | c |

Prophetic Example 13

Psyllid (Insect) Control

ADJ1 would be combined with abamectin to treat citrus mites at a normal use rate according to the label. The ADJ1 would be effectively applied at a rate of about 6 fluid ounces/acre. A reduced population count would be observed at 3, 6, 9 days after treatment (DAT).

Prophetic Example 14

ADJ1 would be combined with spinosad and sprayed on leafminers at a normal use rate according to the label. The ADJ1 would be effectively applied at a rate of about 6 fluid ounces/acre. Reduced population could would be expected to be observed at 3, 6, and 9 days after treatment (DAT).

The invention claimed is:

1. A pesticidal composition efficacious against fungicidal resistant strains of fungi, the pesticidal composition comprising:
at least one strobilurin fungicidal active ingredient; and
benzyl acetate, propylene carbonate, N-methylpyrrolidone, or any combination thereof,
wherein the at least one organic solvent increases the efficacy of the at least one fungicidal active ingredient against the fungicidal resistant strains of fungi by at least about 25% compared to the at least one fungicidal active ingredient alone.

2. The pesticidal composition of claim 1, further comprising water, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof.

3. The pesticidal composition of claim 1, comprising:
from about 5% w/w to about 70% w/w of the at least one fungicidal active ingredient;
from about 39% w/w to about 93% w/w of the at least one organic solvent; and
from about 2% w/w to about 80% w/w of water, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof.

4. An adjuvant composition for increasing the efficacy of a fungicidal active ingredient against fungicidal resistant strains of fungi, the adjuvant composition comprising:
benzyl acetate, propylene carbonate, N-methylpyrrolidone, or any combination thereof,
wherein the adjuvant composition, when combined with at least one strobilurin fungicidal active ingredient, increases the efficacy of the at least one fungicidal active ingredient against fungicidal resistant strains by at least about 25% compared to the at least one fungicidal active ingredient alone.

5. The adjuvant composition of claim 4, further comprising water, citric acid, potassium hydroxide, cocodimethylamine, polyoxyethylene sorbitan monolaurate, at least one emulsifier compound, at least one antifoaming compound, at least one antimicrobial agent, at least one buffer, at least one corrosion inhibitor, at least one dispersing agent, at least one dye, at least one fragrant, at least one freezing point depressant, at least one neutralizing agent, at least one odorant, at least one penetration aid, at least one sequestering agent, at least one spray drift control agent, at least one spreading agent, at least one stabilizer, at least one sticking agent, at least one viscosity-modifying additive, at least one preservative, at least one plasticizer, at least one hydrophobic barrier, at least one UV protectant, at least one water soluble solvent, or any combination thereof.

6. The adjuvant composition of claim 4, wherein the adjuvant comprises:
about 0.0% v/v to about 2.0% v/v water;
about 0.0% v/v to about 2.0% v/v potassium hydroxide;
about 0.0% v/v to about 2.0% v/v citric acid;

about 0.0% v/v to about 2.0% v/v cocodimethylamine;
about 20% v/v to about 99% v/v of at least one organic solvent; and
about 10% v/v to about 70% v/v of at least one surfactant.

7. A tank mix fungicidal composition efficacious against fungicidal resistant strains of fungi, the tank mix fungicidal composition comprising:
at least one strobilurin fungicidal active ingredient;
benzyl acetate, propylene carbonate, N-methylpyrrolidone, or any combination thereof, and
water, spray oil, or a combination of water and spray oil wherein the at least one organic solvent increases the efficacy of the at least one fungicidal active ingredient against the fungicidal resistant strains of fungi by at least about 25% compared to the at least one fungicidal active ingredient alone.

8. The tank mix of claim 7, comprising:
from about 0.2% v/v to about 5% v/v of the at least one fungicidal active ingredient;
from about 0.2% v/v to about 2 v/v % of the at least one organic solvent; and
from about 80% v/v to about 99% of water, spray oil, or a combination of water and spray oil.

* * * * *